(12) United States Patent
Matthews et al.

(10) Patent No.: US 10,130,504 B1
(45) Date of Patent: Nov. 20, 2018

(54) INFLATABLE PROSTHETIC BOOT INSOLE

(71) Applicant: Rodney Matthews, Fairhope, AL (US)

(72) Inventors: Rodney Matthews, Fairhope, AL (US); Dave Cormier, Santa Paula, CA (US)

(73) Assignee: Rodney Matthews, Fairhope, AL (US)

(*) Notice: Subject to any disclaimer, the term of this patent is extended or adjusted under 35 U.S.C. 154(b) by 0 days.

(21) Appl. No.: 15/637,260

(22) Filed: Jun. 29, 2017

Related U.S. Application Data

(60) Provisional application No. 62/356,057, filed on Jun. 29, 2016.

(51) Int. Cl.
| | | |
|---|---|---|
| *A43B 13/20* | (2006.01) |
| *A61F 5/01* | (2006.01) |
| *A43B 17/00* | (2006.01) |
| *A43B 17/03* | (2006.01) |
| *A43B 17/14* | (2006.01) |
| *A43B 7/14* | (2006.01) |
| *A43B 17/18* | (2006.01) |

(52) U.S. Cl.
CPC ............ *A61F 5/0111* (2013.01); *A43B 7/141* (2013.01); *A43B 7/142* (2013.01); *A43B 7/1475* (2013.01); *A43B 13/203* (2013.01); *A43B 17/006* (2013.01); *A43B 17/035* (2013.01); *A43B 17/14* (2013.01); *A43B 17/18* (2013.01); *A61F 5/012* (2013.01)

(58) Field of Classification Search
CPC ..... A43B 13/20; A43B 13/203; A43B 13/206; A43B 17/03; A43B 17/035; A43B 17/006; A61F 5/0111

USPC .............................................................. 36/29
See application file for complete search history.

(56) References Cited

U.S. PATENT DOCUMENTS

| | | | | |
|---|---|---|---|---|
| 4,123,855 A | * | 11/1978 | Thedford | A43B 1/0045 36/153 |
| 4,219,945 A | * | 9/1980 | Rudy | A43B 13/203 36/29 |
| 4,567,677 A | * | 2/1986 | Zona | A43B 13/20 36/28 |
| 4,887,367 A | | 12/1989 | Mackness | |
| 4,991,317 A | * | 2/1991 | Lakic | A41D 19/001 36/29 |
| 5,025,575 A | | 6/1991 | Lakic | |

(Continued)

FOREIGN PATENT DOCUMENTS

| | | |
|---|---|---|
| GB | 129917 A | 7/1919 |
| GB | 1467729 A | 3/1977 |

(Continued)

*Primary Examiner* — Ted Kavanaugh
(74) *Attorney, Agent, or Firm* — James Creighton Wray

(57) ABSTRACT

A foot support for a prosthetic boot has a shape-holding layer and cushion layers on opposite sides of the shape-holding layer. Covers made of nylon and vinyl laminates surround the layers. The vinyl laminates are fused by welding edges of the cover around the foot support. The edge welding surrounds the foot support. An inner parallel welding holds a valve and forms an inflation passage. The inner welding continues around concave curved edges of the shape-holding and cushion layers and terminates where it rejoins the outer welding, forming an inflatable tarsal and metatarsal supporting chamber. A small hard pump has two ends to either increase or reduce pressure in the supporting chamber.

18 Claims, 4 Drawing Sheets

(56) References Cited

U.S. PATENT DOCUMENTS

| | | | |
|---|---|---|---|
| 5,112,560 A | 5/1992 | Moumdjian | |
| 5,996,254 A | 12/1999 | Goven | |
| 6,014,823 A | 1/2000 | Lakic | |
| 6,258,421 B1 * | 7/2001 | Potter | A43B 13/20 36/28 |
| 6,505,420 B1 * | 1/2003 | Litchfield | A43B 13/203 36/28 |
| 6,510,624 B1 | 1/2003 | Lakic | |
| 6,976,321 B1 | 12/2005 | Lakic | |
| 7,017,285 B2 | 3/2006 | Lakic | |
| 7,451,555 B1 | 11/2008 | Lakic | |
| 7,506,543 B2 | 3/2009 | Chiodo | |
| 7,917,981 B1 | 4/2011 | Lakic | |
| 7,959,588 B1 | 6/2011 | Wolpa | |
| 8,863,409 B2 * | 10/2014 | Farina | A43B 13/20 36/29 |
| 8,914,994 B2 * | 12/2014 | James | A43B 13/20 36/28 |
| 2007/0137065 A1 | 6/2007 | Vera | |
| 2012/0073161 A1 | 3/2012 | Doyle | |

FOREIGN PATENT DOCUMENTS

| | | |
|---|---|---|
| WO | 9119430 | 12/1991 |
| WO | 9856272 | 12/1998 |

\* cited by examiner

INFLATABLE PROSTHETIC BOOT INSOLE

This application claims the benefit of U.S. Provisional Application No. 62/356,057 filed Jun. 29, 2016, which is hereby incorporated by reference in its entirety as if fully set forth herein.

BACKGROUND OF THE INVENTION

Prosthetic boots described herein include all air casts and all shells partially surrounding lower legs and feet. The prosthetic boots provide rapid application to feet and legs, accelerate and improve healing of bones and soft tissues compared to rigid casts and are removable for bathing and skin care.

Patients go into boots every day already having plantar fasciitis, heel spurs, metatarsalgia, posterior tibialis and tendonitis. Patients have tried to use their own orthotics, attempting to solve these problems. One patient actually took her own orthotic and placed it in a bed of foam to try and support her foot. Another patient actually took his own ¾ insole and used duct tape to secure it under a boot liner.

A problem of the prosthetic boots exists in foot comfort and arch anchoring. The prosthetic boots anchor lower limbs and feet, provide walkability and access to air and speed circulation and healing. The needs still continue for improved foot sole contacting surfaces sufficient to provide lower foot anchoring and comfort. Especially prominent are the problems of concurrently providing comfort and precise anchoring and stabilizing in the tarsals and metatarsals arch areas of feet. The exact positions and slopes of the natural arches are difficult to attain, and when approached with rigid arches or orthotics provide discomfort to a user.

SUMMARY OF THE INVENTION

The present invention solves the problems of the prior art by providing insoles with stabilized cushioning of the foot and adjustable air pressure bladders for precisely positioning, fitting and holding arch supports while providing comfort from the arch supports to the persons who wear the prosthetic boots.

The new universal inflatable cast boot insoles have one for each size boot and fit right or left boots. The new medical cast boots are useful for ankle fusion and reconstruction patients, tarsal tunnel surgery patients, plantar fasciitis patients, Achilles tendinitis or repair patients, ankle sprain patients and ORIF or non-surgical facture patients. The adjustable arch keeps better alignment during the healing phase. The construction and materials of the insole make it especially appropriate for patients with a history of plantar fasciitis, heel spurs, metatarsalgia and posterior tibialis tendinitis. The invention is created as an accessory item for any and all existing cast boots. It could be billed using a HCPCS code. There are existing reasonable L codes. A PDAC letter could further define an acceptable code. The invention is also used as part of a cast boot and is created as an integral part of an existing cast boot.

The invention provides new insoles for prosthetic boots that include an inflatable arch and has multiple layers for cushioning and stabilizing. Two outer nylon-vinyl layers are cut from sheets having one or more nylon cover layers permanently impregnated or co-bonded with vinyl coatings. The outer sides of the covers are nylon layers for comfort and attractiveness. The nylon-vinyl outer layers provide watertight cover layers and prevent mold and dirt collection. The inner layers have a central polypropylene layer sandwiched between two cushion layers.

The outer covers are peripherally welded around edges. Inner welding areas are spaced inward from the peripheral welds. At one point the continuous inner weld is connected to the outer weld. The outer layers have welding spaces around the edges. The vinyl coated inner layers are weldable and the outer surface is nylon. The outer edge and inner path welding create the bladder and the air channel to the bladder. The space inward from the welding is loose to accept and hold the three inner EVA and PP layers.

The filler tube is formed by the outer cover layers. The bladder is formed by the outer cover layers as well. The outer cover layers are made of a nylon and vinyl material. The insole includes the two outer covers and a polypropylene plastic core laminated between two layers of a shock absorbing foam. Inflation of the arch support uses a bulb and one-way valve. The layers are bonded together by welding the peripheral and inner welding paths of the outer covers, forming the bladder and the filler tube and surrounding and enclosing the inner materials.

The peripheral and inner welds form a semicircular bladder for a tarsals and metatarsals arch support. The inner weld continues from the bladder, forming a welded portion closely parallel to the outer peripheral weld to form an inflation tubular channel. The inflation tube continues around a forefoot support, terminating outwardly in an opening that holds a one-way valve. The bladder is inflatable through the one-way valve and the formed tubular air channel. The inflatable arch support automatically conforms to the position and shape of a natural tarsals and metatarsals arch, while the entire insole provides a comfortable and tough base that avoids collecting mold and dirt.

These and further and other objects and features of the invention are apparent in the disclosure, which includes the above and ongoing written specification, with the claims and the drawings.

DETAILED DESCRIPTION

A prosthetic boot insole is formed of multiple layers.

Figure 1:
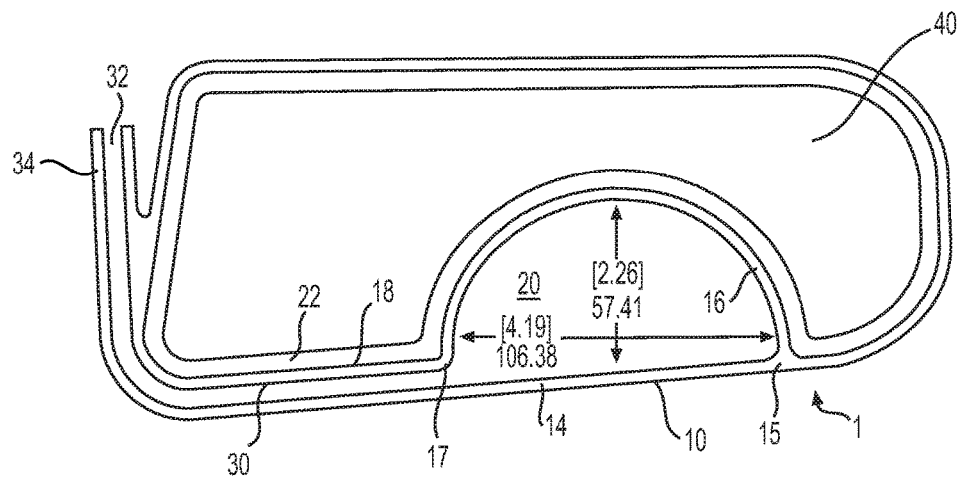
FIG. 1 is a partially assembled view of a prosthetic boot insole.

FIG. 1 shows a view of partially assembled layers for a prosthetic boot insole 1.

A top outer layer 10 has a border 14 for welding. A contiguous semicircular welding path 16 extends from a junction 15 with the outer border 14 around a semicircular area 20 provided for the inflatable arch support and back to a turning point 17 near outer border 14. A contiguous inner welding border path 18 extends forward from an end 17 of semicircular path 16 parallel to the outer border 14, forming a tube area 30. A space 22 inside part of the peripheral border 14, inward from the semicircular path 16 and the longitudinal tube area inner border 18 permits loading and holding three internal layers. Central layer 40 is a general form retaining layer between two identical foam cushioning layers.

The peripheral border 14 and the inner border part 18 together form the tube area 30. An extended valve holding area 32 is formed by extensions 34 of the peripheral border 14.

Figure 2:
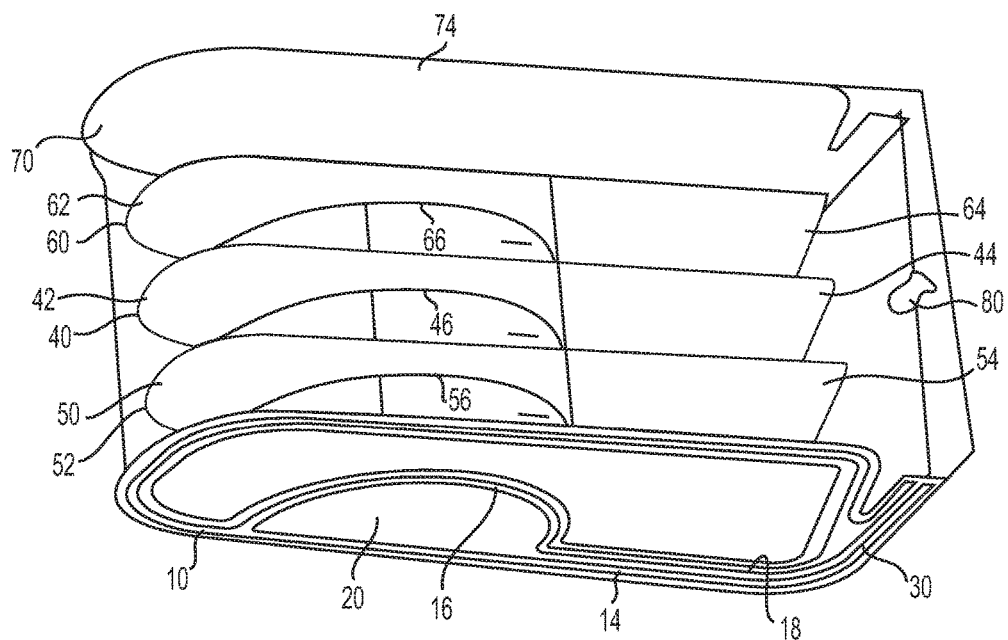
FIG. 2 is an exploded view of the prosthetic boot insole elements.

FIG. 2 is an exploded view of the layers forming the prosthetic boot insole. Outer layer 10 has the weldable border parts 14, 16 and 18 extending around a semicircular inflatable arch support area 20 and a tube area 30.

The general shape-retaining layer 40 is sandwiched between first and second cushion layers 50 and 60. The three layers 40, 50 and 60 have curved heel support areas 42, 52, 62, straight forward areas 44, 54, 64 and general semicircular spaces 46, 56, 66 for accommodating and not interfering with the tarsals and metatarsals arch support area 20 when inflated.

The opposite outer layer 70 has cooperating weldable border and paths 74, 76, 78 for surrounding the inflatable tarsals and metatarsals arch support area 20 and the tube area 30.

In one embodiment, the two outer layers 10 and 70 are formed of a tough nylon-vinyl material which has a nylon mesh and vinyl coating to form a tough waterproof fabric with high resistance to mold, dirt and moisture. Outward facing surfaces of layers 10 and 70 have nylon covers for comfort.

The central layer 40 is formed of pliable and soft form-retaining polypropylene material. The cushion layers 50 and 60 are formed of lightweight, soft and tough EVA ethylene vinyl acetate closed cell foam.

After assembling, the layers are clamped and the peripheral welding border and path areas 14, 16 and 18 of the outer layer 10 and 74, 76 and 78 of the outer layer 70 are heat welded together.

Several sizes of the insoles are produced, including small, medium, large and extra-large to fit available prosthetic boot sizes. The top layer is clearly imprinted with an L or R to indicate placement in the correct right or left prosthetic boot.

In one embodiment, the two outer layers are mirror images, and the insole is reversible with a large L printed on one side and a large R on the other. In that embodiment, the identical upper and lower layers are ballooned and relaxed when formed so that the peripheral welding borders and paths lie flat during clamping and welding and insure even and straight lies within a prosthetic boot. When inflated the lower outer side may lie flat against the boot sole while the upper side balloons to form the tarsals and metatarsals arch support and the tube.

In one embodiment, the top layer 10 and the bottom layer 70 are of similar material and overall shape but are distinct. The top layer 10 is formed in a relaxed or ballooned shape. The lower layer 70 is flat. Thereby the lower layer lies flat on the inside of the prosthetic boot while the upper layer is free to rise. In that embodiment individual left and right insoles are provided.

The one-way valve 80, as shown in FIG. 2, is irremovably inserted in the end 32 of the tube area 30. The valve 80 is inserted in the tube area 30 before the welding and is clamped and welded in place, as shown in FIG. 3.

Figure 3:
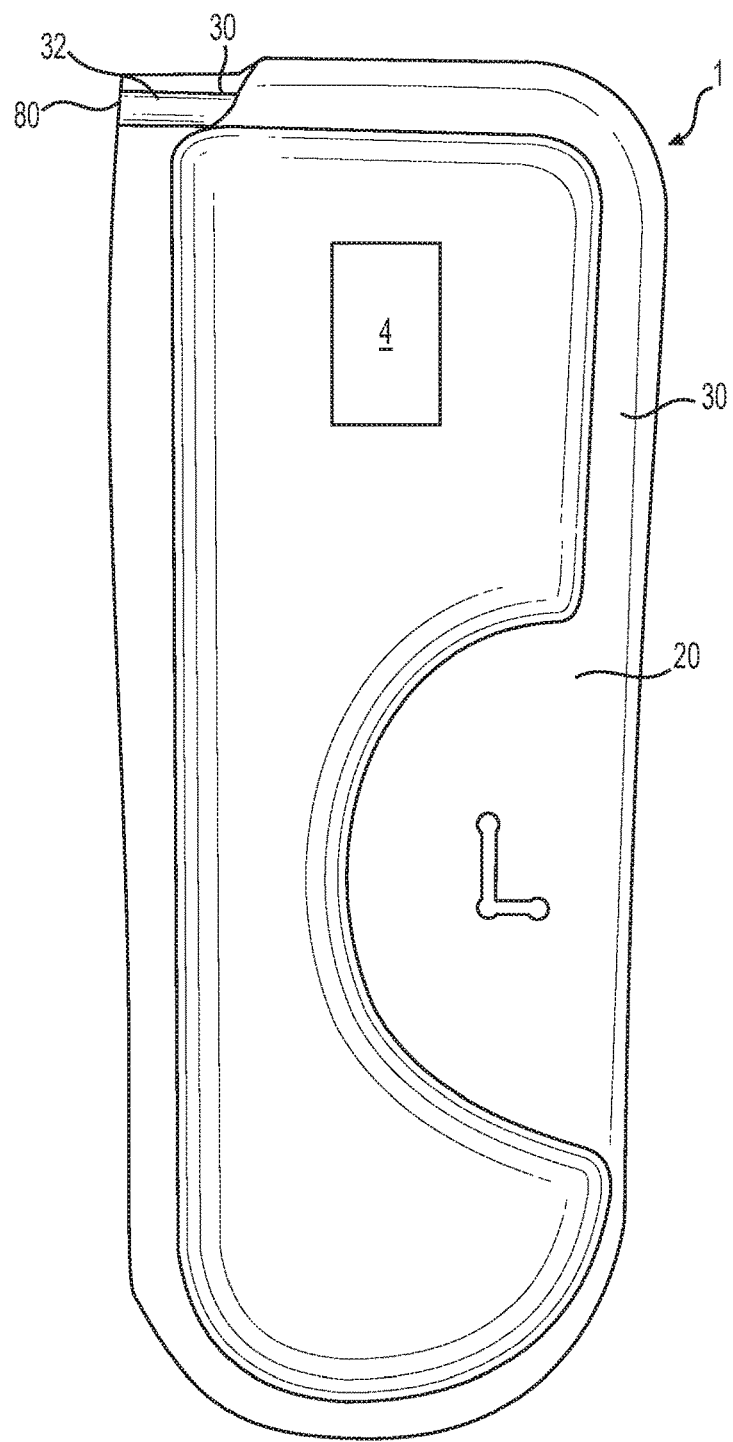
FIG. 3 is a plan view of a prosthetic boot insole showing welding of the layers.

The prosthetic boot insole 1 is shown inflated in FIG. 3.

Figure 4:
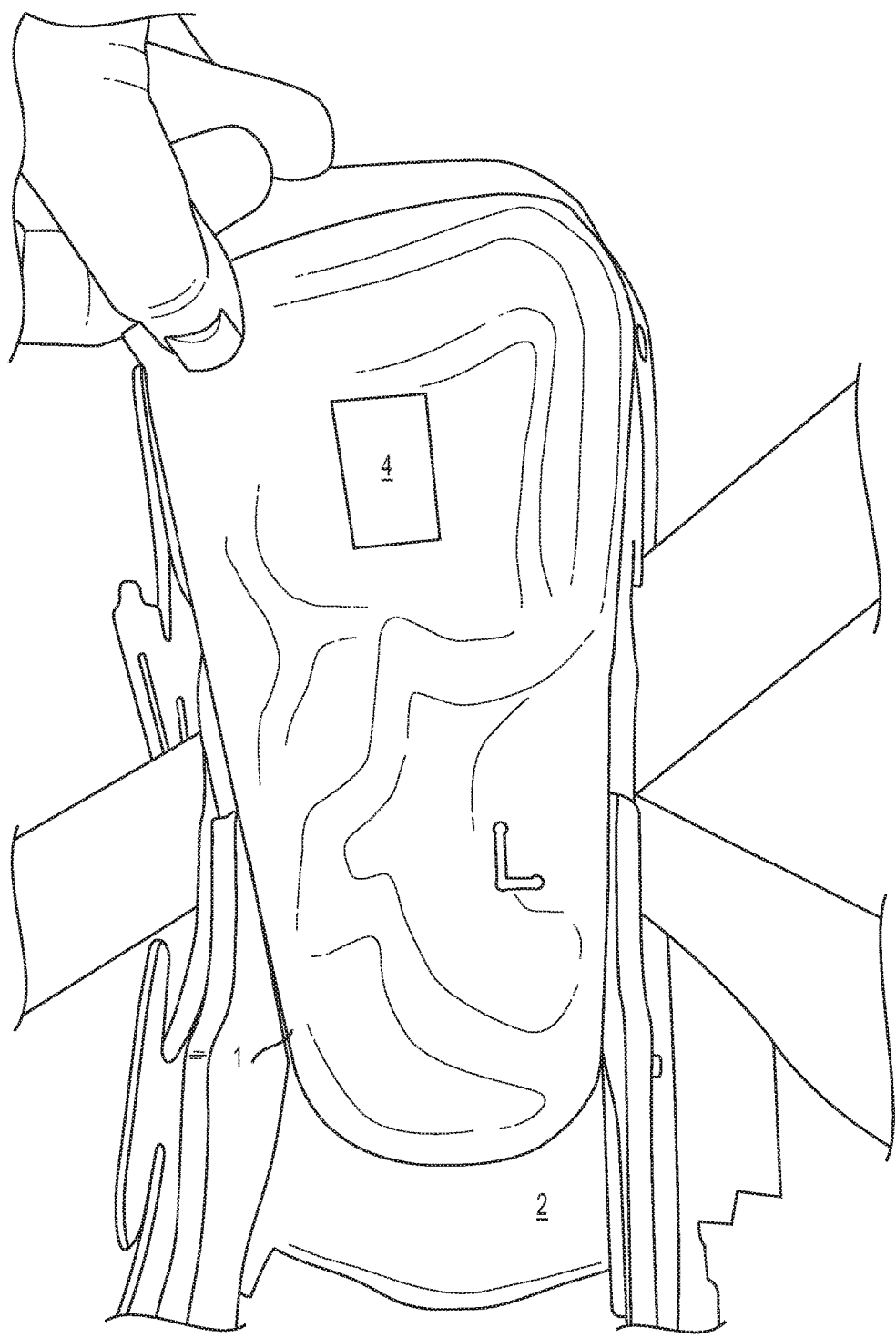
FIG. 4 shows a left boot insole inside a prosthetic boot.

FIG. 4 shows the boot insole 1 deflated or partially inflated and ready for full inflating when placed in a prosthetic boot 2. An adhesive-coated double sided tape 4 shown in FIGS. 3 and 4 positions and secures the new insole on the boot's foot bed. The tape is covered by a difficult-to-remove release layer so that the outer release layer does not easily detach when facing upward. A label identifies the insole and shows the desired inflating pressure range. The insole arch support may be inflated with a hand pump and deflated by insertion of a probe axially in the valve.

The large letter L is printed on or embedded within the outer layer 10. A large letter R is imprinted on the opposite outer layer 70.

In one embodiment of the example shown, the insole 1 is about 260 mm long, 100 mm wide at the front toe area and tapers to about 95 mm at the heel area. The inflatable tarsal and metatarsal arch support area is about 110 mm long and about 6 mm wide. The border areas for welding may be about 3 mm wide, and the tube area may be about 6 mm wide.

The central stabilizing polypropylene layer 40 is about 1.5 mm thick. The cushion layers 50 and 60 have about 1 mm thickness.

Figure 5:
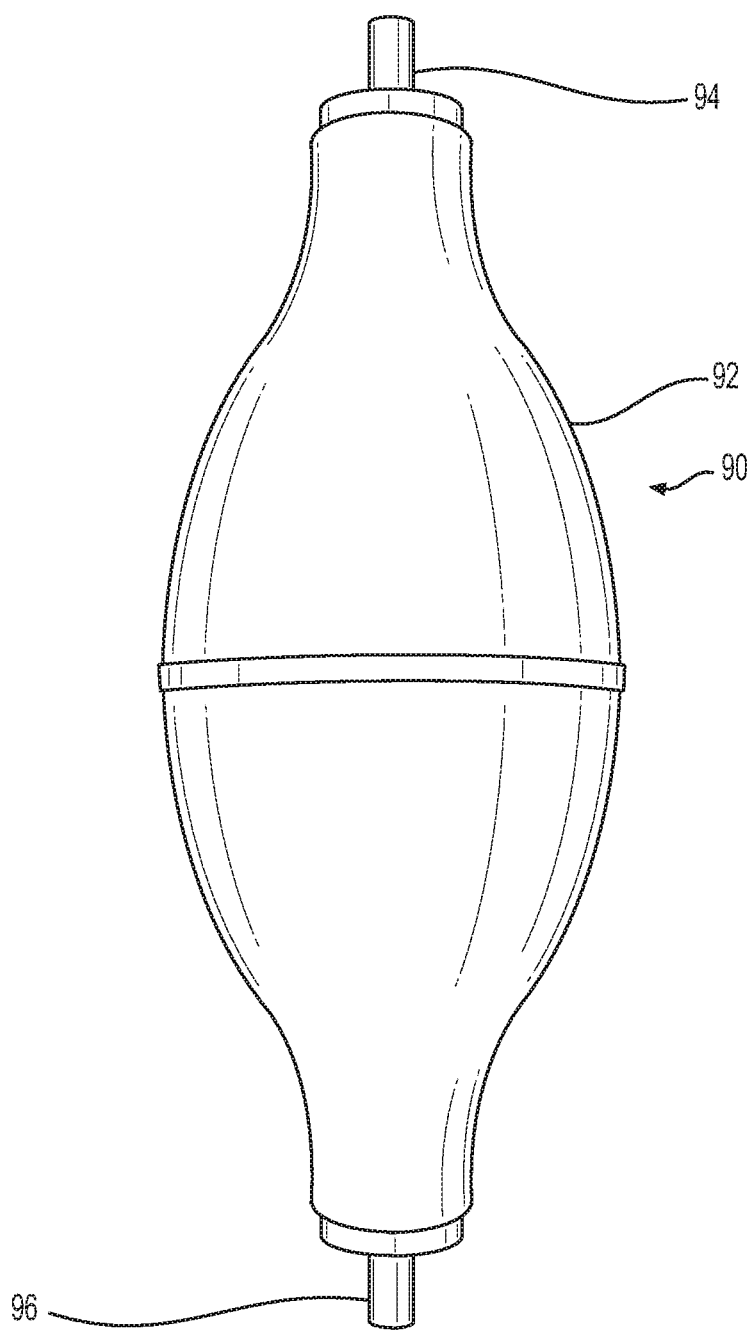
FIG. 5 shows a squeezable bulb pump for inflating and deflating the arch support in the insole.

An inflating and deflating squeezable bulb hand pump 90 is shown in FIG. 5. The clear end 94 of the squeezable bulb 92 is inserted in valve 80 for inflating the arch support of insole 1. The black end 96 is inserted in valve 80 for deflating the arch support. A pressure gauge (not shown) may be connected between the squeezable bulb 90 and the valve 80 for precisely controlling the pressure in the inflatable arch support.

While the invention has been described with reference to specific embodiments, modifications and variations of the invention may be constructed without departing from the scope of the invention, which is defined in the following claims.

We claim:

1. Apparatus comprising:

An inflatable insole adapted for placement under a foot inside a bottom of a prosthetic boot, the inflatable insole further comprising:

an inner shape-retaining layer, cushion layers positioned outward from the shape-retaining layer, the inner shape-retaining layer and the cushion layer having rounded heel supporting areas and elongated phalanx support areas, and having connecting areas extending between the heel support areas and the phalanx support areas, the connecting areas having outer side support areas connecting the heel and phalanx support area and inward curved edges opposite the outer side support areas, leaving a space having inward curved edges and an outer straight edge, the inward curved edges having first ends adjacent the heel support areas and second ends adjacent the phalanx support areas providing a curved and straight sided space along an inner side opposite the outer side support areas, outer cover layers being configured for extending outward beyond the heel support areas and the phalanx support areas and the outer straight edge, the outer cover layers having edge seals extending around the heel support areas, the phalanx support areas and the outer side support areas, the outer straight edge and the inward curved edges, wherein the edge seals are configured for forming an inflatable chamber in a space between the curved inward edges and the outer straight edge.

2. The apparatus of claim 1, wherein the outer layers are laminates having impervious outer layers and fusible inner layers.

3. The apparatus of claim 1, wherein the outer cover layers are laminated nylon and vinyl layers.

4. The apparatus of claim 1, having one or more nylon layers permanently impregnated or co-bonded with vinyl coatings.

5. The apparatus of claim 1, wherein the vinyl coated inner layers are weldable.

6. The apparatus of claim 1, wherein the inner shape-retaining layer is polypropylene.

7. The apparatus of claim 1, wherein the cushion layers are ethylene vinyl acetate.

8. The apparatus of claim 1, wherein the edge seals are welds.

9. The apparatus of claim 1, wherein the edge seals further comprise parallel edge seals configures for forming a filler passage, wherein the edge seals further comprise a divergent portion of the edge seals leading around the inward curved edges, and a second edge seal straight portion of the edge seals and extending between a first end and to a second end of the inward curved edges adapted for forming an inflatable tarsal and metatarsal support, and wherein the seals further provide a gap in the parallel portions configured for providing a port for inflation of the curved and straight sided tarsal and metatarsal support along the inner side opposite the curved inner side and between the outer layers.

10. The apparatus of claim 9, further comprising a one-way value in the gap between the parallel edge seals.

11. Apparatus comprising:
an inflatable prosthetic boot insole, further comprising:
an inner shape forming layer,
at least one foot cushioning layer overlying the shape forming layer, the inner shape forming layer and the at least one foot cushioning layer having heel edges, outer side edges, toe supporting edges and inner side edges,
the inner side edges having inward curved edges extending outward beyond the edges of outer layers overlying the underlying the inner shape forming layer and the at least one foot cushioning layer,
the outer layers having first joinings around the heel edges, outer side edges, toe supporting edges and inner side edges,
the inner side edges having inward curved edges except for a small gap,
the outer layers having second joinings extending from a first end of the inward curved edges and extending at positions widely spaced from a remainder of the curved edges and then closely spaced from the first joinings and terminating at the gap,
a valve mounted in a closely spaced place between the first joining and the second joining,
widely spaced portions of the first joining and the second joinings configured for forming an inflatable tarsal and metatarsal support,
the closely spaced first and second joinings extending from the gap to a second end of the curved edges and then to a first end of the curved edges where the first and second joinings of the outer layer meet, and further comprising a valve between the closely spaced first and second joinings for controlling pressure in the inflatable tarsal and metatarsal support.

12. The apparatus of claim 11, wherein the outer layers are laminates having impervious outer layers and fusible inner layers.

13. The apparatus of claim 11, wherein the outer cover layers are laminated nylon and vinyl layers.

14. The apparatus of claim 11, having one or more nylon layers permanently impregnated or co-bonded with vinyl coatings.

15. The apparatus of claim 11, wherein the vinyl coated inner layers are weldable.

16. The apparatus of claim 11, wherein the inner shape-retaining layer is polypropylene.

17. The apparatus of claim 11, wherein the cushion layers are ethylene vinyl acetate.

18. The apparatus of claim 11, wherein the edge seals are welds.

* * * * *